United States Patent
Ellingsen et al.

(10) Patent No.: US 7,048,870 B1
(45) Date of Patent: May 23, 2006

(54) METALLIC IMPLANT AND PROCESS FOR TREATING A METALLIC IMPLANT

(75) Inventors: Jan Eirik Ellingsen, Bekkestua (NO); Gunnar Rölla, Oslo (NO)

(73) Assignee: AstraZeneca AB (SE)

( * ) Notice: Subject to any disclaimer, the term of this patent is extended or adjusted under 35 U.S.C. 154(b) by 322 days.

(21) Appl. No.: 09/602,528

(22) Filed: Jun. 23, 2000

Related U.S. Application Data

(63) Continuation-in-part of application No. 08/446,675, filed as application No. PCT/SE94/01225 on Dec. 19, 1994, now abandoned.

(30) Foreign Application Priority Data

| Dec. 20, 1993 | (SE) | ..................................... 9304209 |
| Jun. 3, 1994 | (SE) | ..................................... 9401928 |

(51) Int. Cl.
  *B44C 1/22* (2006.01)
  *C03C 15/00* (2006.01)
  *C03C 25/68* (2006.01)
  *C23F 1/00* (2006.01)
  *C25F 3/00* (2006.01)

(52) U.S. Cl. .................... 216/109; 216/100; 623/23.55

(58) Field of Classification Search ................ 216/100, 216/108, 109; 623/901, 16.11, 20.17, 23.29; 433/201.1
See application file for complete search history.

(56) References Cited

U.S. PATENT DOCUMENTS

| 3,043,758 | A | | 7/1962 | Machu et al. ................ 204/145 |
| 4,042,679 | A | * | 8/1977 | Gaffar .......................... 424/54 |
| 4,746,532 | A | * | 5/1988 | Suzuki et al. ................ 428/336 |
| 4,874,434 | A | * | 10/1989 | Riggs, Jr. ..................... 134/28 |
| 5,039,546 | A | | 8/1991 | Chung et al. |
| 5,456,723 | A | * | 10/1995 | Steinemann et al. .......... 606/76 |
| 5,603,338 | A | * | 2/1997 | Beaty .......................... 128/898 |
| 5,876,453 | A | | 3/1999 | Beaty .......................... 623/16 |

FOREIGN PATENT DOCUMENTS

| DE | 303425 | 5/1995 |

(Continued)

(Continued)

OTHER PUBLICATIONS

Nishino et al., "Experimental Study on Hydroxyapatite Soaked in Sodium Fluoride", STN International File CA Chemical Abstracts, vol. 116, No. 24, 65(1-2), 1199-1210, Jun. 15, 1992.

(Continued)

*Primary Examiner*—Parviz Hassanzadeh
*Assistant Examiner*—Roberts Culbert
(74) *Attorney, Agent, or Firm*—Fish & Richardson P.C.

(57) ABSTRACT

A process for treating a metallic implant consisting essentially of treating the metallic implant with a solution of hydrofluoric acid, which solution has a pH between 1.6 and 3.0.

14 Claims, 6 Drawing Sheets

FOREIGN PATENT DOCUMENTS

| | | |
|---|---|---|
| EP | 0040461 A1 | 11/1981 |
| EP | 0202031 A3 | 11/1986 |
| JP | 3-146679 | 6/1991 |
| JP | 3146679 | 6/1991 |
| JP | 03146679 A * | 6/1991 |
| WO | WO 94/13334 | 6/1994 |
| WO | WO 9413334 A1 * | 6/1994 |
| WO | WO 95/17217 | 6/1995 |

OTHER PUBLICATIONS

International Search Report, (1 page).

Braun et al., "Surface Characterization of Titanium and Titanium Alloys part 2: Effect on TI-6A 1-4V Alloys . . . ", Technical Report AFML-TR-76-29, Part II, Final Rept. for Period Jul. 1975-Feb. 1976, Air Force Mat. Lab, May 1976.

Panagopoulos, "A Surface Study of Chemically Etched Titanium", J. of the Less-Common Metals, 134:237-243, 1987.

International Preliminary Search Report, (7 pages).

Abstract of JP-3146679 Published Jun. 21, 1991.

Sax et al, "Howley's condensed Chemical Dictionary", 11 Ed. (1987) p. 893.

* cited by examiner

US 7,048,870 B1

METALLIC IMPLANT AND PROCESS FOR TREATING A METALLIC IMPLANT

This application is a continuation-in-part of U.S. Ser. No. 08/446,675, filed Sep. 20, 1996 now abandoned, which is a national phase of application PCT/SE94/01225, filed Dec. 19, 1994, which are hereby incorporated by reference.

Under 35 U.S.C. 119(a), this application claims the benefit of Swedish Application No. 9401928-8, filed Jun. 3, 1994, and Swedish Application No. 9304209-1, filed Dec. 20, 1993.

TECHNICAL FIELD

The present application relates to biocompatible metallic bone implants, preferably made of titanium or an alloy thereof, and to a method for treating metallic implants to enhance their biocompatibility.

BACKGROUND

A commonly used method for implanting metallic implants into bone tissue is a two stage procedure involving in a first operation surgically placing the implant into the bone tissue, where it is then allowed to rest unloaded and immobile for a healing period of three months or more in order to allow the bone tissue to grow onto the implant surface so as to permit the implant to be well attached to the bone tissue, the cut in the soft tissue covering the implant site being allowed to heal over the implant, and in a second operation opening the soft tissue covering the implant and attaching the functional parts to the implant. This two-stage procedure is often used in connection with dental implants, one reason being that it minimized the risk of infection of the implant site from the oral cavity. In some orthopedic applications the above two-stage surgery may not be necessary since most orthopaedic implants do not penetrate the soft tissue. A prolonged healing period is however still considered necessary since any movements of the implant in the weeks and months following surgery may endanger the final attachment of the implant to the bone tissue.

The above procedure is for instance described in Branemark et al: "Osseointegrated Implants in the Treatment of Edentulous Jaw, Experience from a 10-year period", Almquist & Wiksell International, Stockholm—Sweden.

However, the fact that the implant may not be loaded means that the functional parts of the implant may not be attached to the implant and/or used during the healing period of three months or more. In view of the discomfort associated with this, it is desirable to minimize the time period necessary for the above-mentioned first stage and in some cases, for instance in certain orthopaedic application, substantially dispense with said first stage and perform the entire implantation procedure in a single operation.

An object of the present invention is to provide an implant with improved rate of bone tissue attachment such that the post-surgery healing period described above may be reduced.

Some of the metals or alloys used for bone implants are capable of forming a strong bond with the bone tissue, a bond which may be as strong as the bone tissue per se, sometimes even stronger. The most notable example of this kind of metallic implant material is titanium and allows of titanium whose properties in this respect have been known since about 1950. This bond between the metal and bone tissue has been termed "oseointegration" by Brånemark et al.

Although this bond between titanium and bone tissue is comparatively strong, in some applications it is desirable to enhance the bond between metal and bone tissue.

There are to date several methods for treating implants made of titanium in order to obtain a better attachment of the implant. Some of these involve altering the topography of the implant, for example by creating relatively large irregularities on the implant surface in order to obtain a better mechanical retention and to increase the area of attachment, by for example plasma spraying, blasting or etching. Although the retention may be improved, the time necessary for the osseointegration process may be longer since the bone tissue would have to grow into the irregularities in the surface.

Other methods involve altering of the chemical properties of the implant surface. For example one such method involves the application of a layer of ceramic material such as hydroxyapatite to the implant surface, inter alia in order to stimulate the regeneration of the bone tissue. Ceramic coatings however may be brittle and may flake or break off from the implant surface, which may in turn lead to the ultimate failure of the implant.

U.S. Pat. No. 4,330,891 could perhaps be said to combine each of the above, in that the provision of an element with a micro-pitted surface which micro-pits are within a certain diameter range, is said to effect improved properties as regards acceptance of the carrier element, and primarily improved durability of the healthy ingrowth of the element due to its biological quality.

A further object of the invention is to provide an implant forming a stronger bond with the bone tissue.

Short description of the inventive concept.

It has been found that the desired metallic implant may be obtained by treating a metallic surgical implant with an aqueous solution of hydrofluoric acid.

SHORT DESCRIPTION OF THE APPENDED DRAWINGS

FIG. 1 is diagram illustrating the pushout force as well as the fluorine and oxygen content of an implant surface treated with 0.2% HF as a function of the treatment time.

FIG. 2 is a SEM photograph of an implant surface treated with 0.2% HF for 30 seconds, in a magnification of 10 000 times, FIG. 3 is the implant surface in FIG. 2, in 52 000 times magnification, FIG. 4 is a SEM photograph of an implant, in 10 000 times magnification, having been treated with 0.2% HF for 90 seconds, FIG. 5 is the surface of FIG. 4 in 52 000 times magnification.

THE INVENTION

Figure 1:
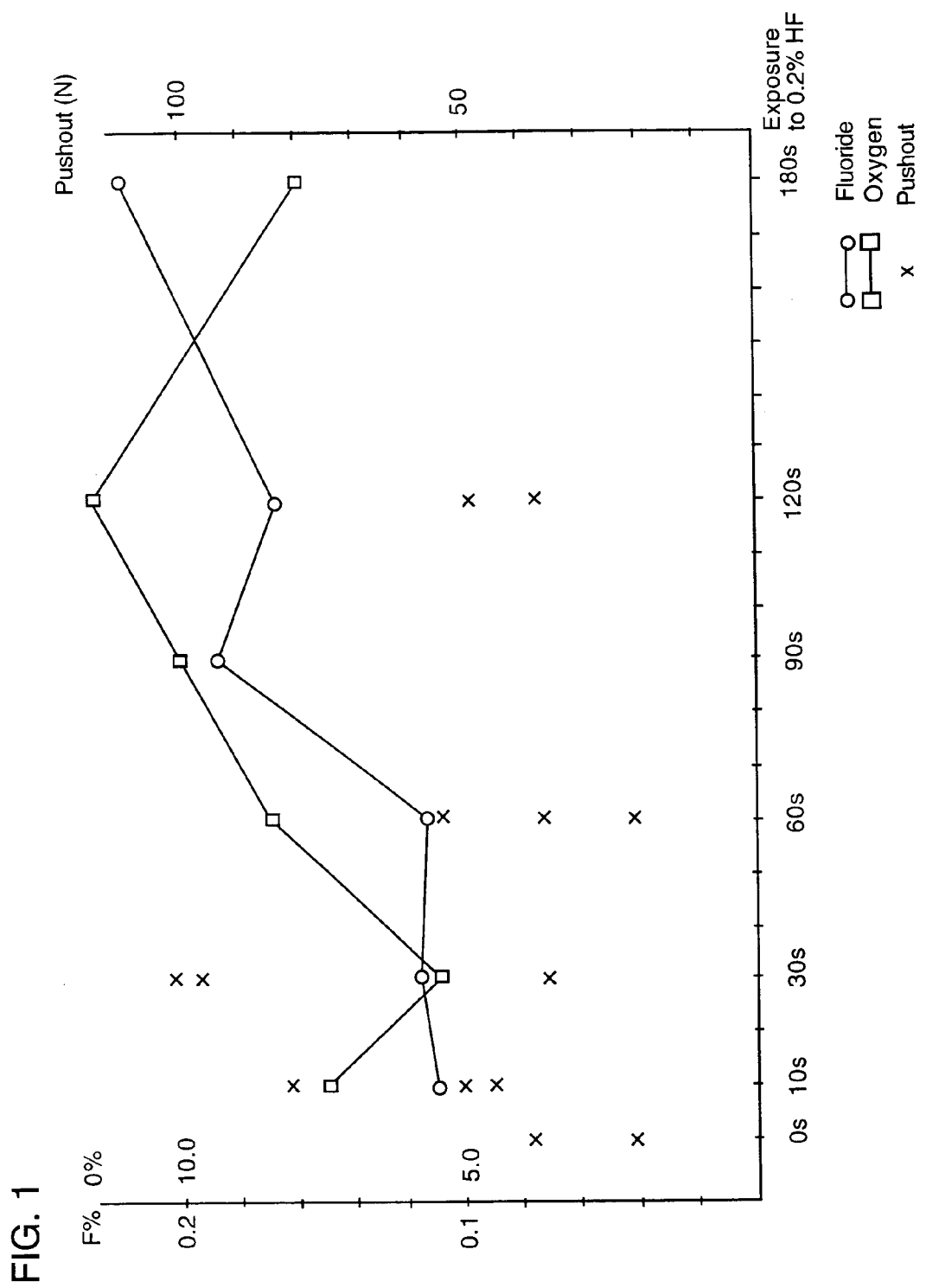

Accordingly, in a first aspect the present invention provides a process for the treatment of a metallic implant comprising treating the metallic implant with an aqueous solution of hydrofluoric acid, which solution is of pH 1.6 to pH 3.

Alternatively stated in terms of concentration, the present invention provides a process for the treatment of a metallic implant comprising treating the metallic implant with an aqueous solution of hydrofluoric acid of concentration up to 3.0%

Preferably the metallic implant is made of commercially pure titanium or an alloy of titanium. The implants may be standard, blasted or other.

Preferably, the concentration of hydrofluoric acid is 0.01% to 3.0% such as 0.1% to 2.0%. Most preferably the concentration of hydrofluoric acid is about 0.2% to about 2.0% especially 0.2% to 0.5% and most preferably about 0.2%.

The treatment of the present invention may be carried out for any suitable length of time. Preferably the treatment is carried out for at least 10 seconds such as 10 seconds to 6 hours, for example 10 seconds to 2 minutes such as 10 s to 50 s, or 30 s, 60 s, or 2 minutes.

The treatment may be carried out in any suitable manner, for example by immersing the implant in the treatment solution for a period of time, and with or without agitation. Varying temperatures may be employed; parameters such as temperature and time may be selected according to the concentration of the treatment solution and the other process parameters. The treatment is conveniently carried out at standard pressure, but elevated pressures may be used where desired. Preferably, treatment is carried out at around standard temperature and pressure.

In a preferred embodiment the present invention provides a process for the treatment of a metallic implant comprising treating the metallic implant with a 0.1–2.0% aqueous solution of hydrofluoric acid at room temperature for a period of up to 3 minutes.

The treatment solution of the present invention may be simply prepared, by duluting concentrated HF with distilled water.

Prior to treatment, the implant material may be cleaned by standard techniques such as are well known in the art.

After treatment, the implant material may be washed in distilled water and kept under sterile conditions.

Implants treated in accordance with the present invention show a strong contact with bone, as demonstrated in "push-out" tests described herein, and a high degree of bone contact in the spongiosa cancellous region. New bone will form on the implant surface in the cancellous region and will more or less cover the implant in this area. Such a response is not observed in untreated control groups. The degree of bone contact indicates bone growth in the spongiosa cancellous region.

The process specified therefore beneficially effects the surface of the implant so as to improve the biocompatibility (specifically the rate of bone tissue attachment and strength or bonding) of the implant. While we do not wish to be limited to the expression of theories herein, the improved biocompatibility is thought to be due, at least in part, to fluoride being retained on the surface of the implant. As such, treatments other than with hydrofluoric acid, which provide fluoride ions, could be expected to have some effect on the biocompatibility of metallic implants. Treatment with sodium fluoride is known from our prior application WO 94/13334. In a second aspect this invention therefore provides a process for treating a metallic implant comprising treating the implant with an aqueous solution containing fluoride ions in a concentration of up to 3%, said aqueous solution being free of sodium ions. The preferred treatment parameters correspond to those preferred in the hydrofluoric acid treatment described herein.

Preferably no significant etching of the implant surface occurs with the present treatment. Most preferably, there is substantially no etching of the implant surface.

Thus, metallic implants treated according to the invention preferably have essentially the same morphology as the surfaces of the implants before said treatment. By "essentially the same morphology" is intended that the surfaces of the implants only undergo minor morphological changes or no morphological changes at all during the chemical treatment according to the invention.

Implants treated by the process of the present invention are also provided herein. Therefore in a third aspect the present invention provides a metallic implant which has been treated with an aqueous solution of hydrofluoric acid according to the processes described herein.

As stated hereinabove, the beneficial effect of the present invention is thought to be related to fluoride being retained on the surface of the treated implant. The treatment described is a surface treatment which affects the surface properties of the implant although at this stage it is not possible to define the surface characteristics of the treated implant more than to say that the desired characteristics are provided by the present process.

In fourth aspect therefore the present invention provides a metallic implant having a surface equivalent to the surface of an implant which has been treated with an aqueous solution of hydrofluoric acid according to the processes described herein.

The metallic implant according to the invention or treated according to the invention may be an implant constituted of only a metal or a metal alloy. It may also be an implant constituted of a metal or a metal alloy covered at the surface, at least partially, by a layer, preferably a thin layer, of an oxide.

In a fifth aspect the present invention thus provides a process for treatment of metallic implants, such as implants of titanium or a titanium alloy, covered at least partially with an oxide layer.

When a metallic implant, and especially an implant of titanium or titanium alloy, is exposed to surrounding air, a titanium oxide layer is often formed on the surface due to oxidation of the metal, such as titanium, by the oxygen in the air.

This oxide covered metallic implant is treated with the above described process in order to provide a fluoride or fluorine containing layer on the surface of the implant. In order to obtain this fluoride or fluorine containing surface it is possible to use any source of fluoride ions or fluorine, such as an aqueous solution comprising fluoride ions, provided that the solution is free of sodium and sodium ions. It is thus possible to use a solution of hydrofluoric acid, or of a fluoride such as fluoride selected from the group consisting of lithium fluoride, cesium fluoride, potassium fluoride, ammonium fluoride and stannous fluoride, or a combination of several of these sources.

The treatment period needed in order to obtain the desired content of fluoride or fluorine in the surface layer is due to the thickness of the oxide layer on the metallic core of the implant.

According to a sixth aspect a metallic implant with a fluoride or fluorine containing surface may be further treated with a solution containing calcium ions, in order to further improve the biocompatibility.

This treatment with calcium ions leads to the deposition of calcium onto the surface of the metallic implant or onto the oxide layer on the metallic implant.

Preferably, the metallic implants or the oxide-covered implants are placed or dipped in the solution for an appropriate period of time, such as a period of 10 seconds to 10 minutes.

As calcium ion source it is possible to use any calcium containing compound that provides calcium ions in solution. The solution containing calcium ions may thus be an aqueous solution of calcium fluoride, calcium phosphate, calcium acetate, calcium chloride or any other water-soluble calcium salt. The solution may either be a diluted or saturated solution.

Optionally, this calcium deposition may be obtained through naturally occurring biological processes once the implant is inserted into the bone tissue. Since calcium is present in the body, calcium will be deposited on the surface of an implant once it is implanted into the body. However, this natural calcium deposition process is slower than the above described treatment. According to this aspect of the invention it is preferable to perform the calcium treatment before implantation.

Another was of describing the effect of the present treatment is by means of the induction of calcium phosphate precipitation. This is an in vitro test described in "Damen, Ten Cate, Ellingsen, Induction of Calcium Precipitation by Titanium dioxide, Journal of Dental Research, October 1991". In this method an implant is immersed in a saturated solution of calcium phosphate.

Depending on the surface, precipitation of calcium onto the implant occurs. The concentration of Ca++ is monitored and the time delay (the induction time) until precipitation occurs is measured. The rationale behind this test is the assumption that there is a correlation between the affinity of the implant surface towards the calcium ions and the biocompatibility of the implant surface in bone tissue. Implants treated in accordance with the present invention show an affinity to calcium ions in this test. Accordingly, in a fourth aspect the present invention provides an implant treated with hydrofluoric acid in accordance with the present invention, which implant precipitates calcium ions from a saturated solution of calcium phosphate.

The following Examples illustrate the invention.

EXAMPLES

Example 1

Seven surgical implants, commercially pure (c.p.) titanium, 5 mm in length and generally conical in shape having a diameter at one end of 3 mm and at the other end 2 mm, were prepared by machining using a "Maximat super 11" (TM) turning lathe. Therefore the area of the conical sides of the implant, i.e. the part of the implant to be located in the bone, is 39 mm$^2$.

Each implant was cleaned according to a well-known cleaning procedure involving the following steps:

1. Treatment with trichloroethylene with ultrasonic treatment, for 15 minutes.

2. Rinsing in absoute ethanol, for 10 seconds.

3. Three successive treatments with ethanol with ultrasonic treatment, each for 10 minutes.

Each cleaned implant was sterile packaged in a Mediplast (TM) sterile envelope, and autoclaved in a Citomat 162 (TM) (LIC Company) autoclave, at 120 C for 30 minutes.

A HF bath was prepared simply by diluting concentrated HF with distilled water, to give 0.2% solution. The pH of the bath was 2.1.

Seven implants, prepared, cleaned, sterile packaged and autoclaved exactly as described above, were removed from their sterile packages, placed in the HF treatment bath and left there for two minutes. Thereafter each was washed three times in a bath of distilled water, for periods of 30 seconds each wash. After being allowed to dry at room temperature, each implant was transferred to a Mediplast (TM) sterile envelope to await surgical implantation.

Implant Study

Chinchila rabbits were used as test animals. The rabbits were randomly distributed regarding sex, but all had a weight of 2.5 kg at the start of the study. Each animal was sedated by injection using a combination of fluanozonium 1.0 mg/kg and fentanylium 0.02 mg/kg (Hypnorm, Jannsen Pharmaceuticals, Belgium) and locally anesthetized with xylocaine/adrenaline (AB Astra). Two cavities were drilled in each rabbit's right ulna, using standardized bores designed to provide cavities into which the conical implants would exactly fit. Treated and untreated implants were placed in the cavities of each rabbit, using titanium tweezers so as to avoid the influence of other metals, and left for sixty days.

At the end of sixty days the rabbits were sacrificed by injection with pentobarbital natrium, and the ulna's removed and placed in sterile physiological saline to await a "push-out" test the same day.

An Instron model 1121 tensile testing machine (Instron, U.K.) inter alia comprising a support jig and a ram adjusted for a load range of 0–200 N, was employed to measure the force needed to separate each implant from bone. Milling tracks, to fit the support jig, were made in the specimen to be tested, in the bone surrounding the larger end of the implant, and the specimen was placed on the support jig. The ram lowered at a speed of 1 mm/min., and the force required to separate the implant from the bone was recorded.

This recorded force gives a direct assessment of the strength of connection of implant and bone, the higher the required force the stronger the connection.

The results are recorded in Table 1.

TABLE 1

| Recorded force (N) | | | |
|---|---|---|---|
| Untreated implants | | Treated implants | |
| 1 | 18.1 | 1 | 84.1 |
| 2 | 59.2 | 2 | 96.0 |
| 3 | 44.7 | 3 | 64.2 |
| 4 | 39.2 | 4 | 62.7 |
| 5 | 59.5 | 5 | 64.9 |
| 6 | 6.0 | 6 | 89.5 |
| 7 | 8.5 | 7 | 89.5 |
| mean | 33.6 | mean | 78.7 |

The much greater strength of bone connection with implants treated in accordance with the present invention is apparent from the above.

Histological examination demonstrated that the implants according to Example 1 were surrounded even in the ulna's spongiosa by a thick layer of newly formed bone which was in close contact with the implants. In contrast the untreated implants, i.e. those according to the Comparative Examples, were only partly covered, by a thin bone layer, in the spongiosal area.

Example 2

Reference implants were made of titanium grade 3, and were made by turning at an average speed of about 7 meters per minute. No cutting fluid was used. The cutting tool was made of high speed steel.

The reference implant surface was cleaned by a standard cleaning procedure involving the following steps:

1. Treatment with trichloroethylene with ultrasonic treatment for 15 minutes.

2. Rinsing in absolute ethanol for 10 seconds.

3. Three successive treatments with ethanol with ultrasonic treatment, each for 10 minutes. Each cleaned implant should then be sterile package in a Mediplast (TM) sterile envelope and autoclaved in a Citomat 62 (TM) (LIC Company) autoclave at 1200 C for 30 minutes.

The result of an experiment in which the force necessary for removing (pushing out) substantially conical, unthreaded implants treated in 0.2% aqueous solution of hydrofluoric acid at room temperature for different time periods is illustrated in the diagram in FIG. 1. The implants had been manufactured to have a diameter of 2 mm at one end, 3 mm at the other end and an overall length of 5 mm and were made from titanium grade 3 and cleaned and sterilized in accordance with the above procedures for treating the reference implant surface. The treatment times were 10 seconds, 30 seconds, 60 seconds, 90 seconds, 120 seconds and 180 seconds. Pushout tests were made and the pushout forces were marked in the diagram for each treatment time except 90 and 180 seconds. The values for an untreated control specimen are also given in the diagram as having a treatment time of 0 seconds.

Each value for the pushout test results are a mean of the values for four implants implanted in the tibia of a respective rabbit and left to heal into the bone tissue for two months.

The reference implants were also treated in the way described above. The content of fluorine and of oxygen as measured in the surface of the treated implants are marked in the diagram for each treatment time.

An Instron model 1121 tensile testing machine (Instron, U.K.) set to the same parameters as the machine in Example 1 was used and the contents of fluorine and oxygen were measured by means of an Electron microprobe (CAMECA camebax) at SINTEF/SI in Oslo. The results as measured with this equipment were

|         | F %  | O %  |
|---------|------|------|
| 0 sec   | 0.01 | 5.1  |
| 10 sec  | 0.15 | 5.5  |
| 30 sec  | 0.11 | 5.8  |
| 60 sec  | 0.17 | 5.7  |
| 90 sec  | 0.2  | 9.4  |
| 120 sec | 0.23 | 8.4  |
| 180 sec | 0.16 | 11.0 |

The diagram In FIG. 1 illustrates higher values for the pushout tests resulting from treatment times varying between 10 and 50 seconds with a peak value at 30 seconds. The values for the remaining treatment times and the untreated control specimens are lower although the treated implants generally have higher values than the untreated ones. The values for the oxygen (5.5 to 5.8%) and fluorine content (0.11 to about 0.15%) of the surface of the implants for the treatment times between 10 and 50 seconds are lower than the corresponding values for the other treatment times.

The pushout tests were made after a time period which was as short as two months. The rapid increase of the strength of the bond results in that the healing period necessary for reaching a given strength of the bone is shortened. The use of the treatment according to the invention thus facilitates the use of one-stage surgical procedures particularly in orthopaedics, since the time the patient must remain inactive is shortened.

Figure 2:

FIG. 2 illustrates how the implant surface seems to be largely unaffected by the treatment involving a HF-concentration of 0.2% and a treatment time of 30 sec, no effect being discernable in a magnification of 10 000 times (the original tooling marks not being affected at all). This photograph shold be compared with the photograph in FIG. 4, in 10 000 times magnification, showing a surface which has been treated longer (90 seconds) in 0.2% HF and in which the marked change in the surface by the treatment in question is illustrated.

Figure 3:
Figure 4:
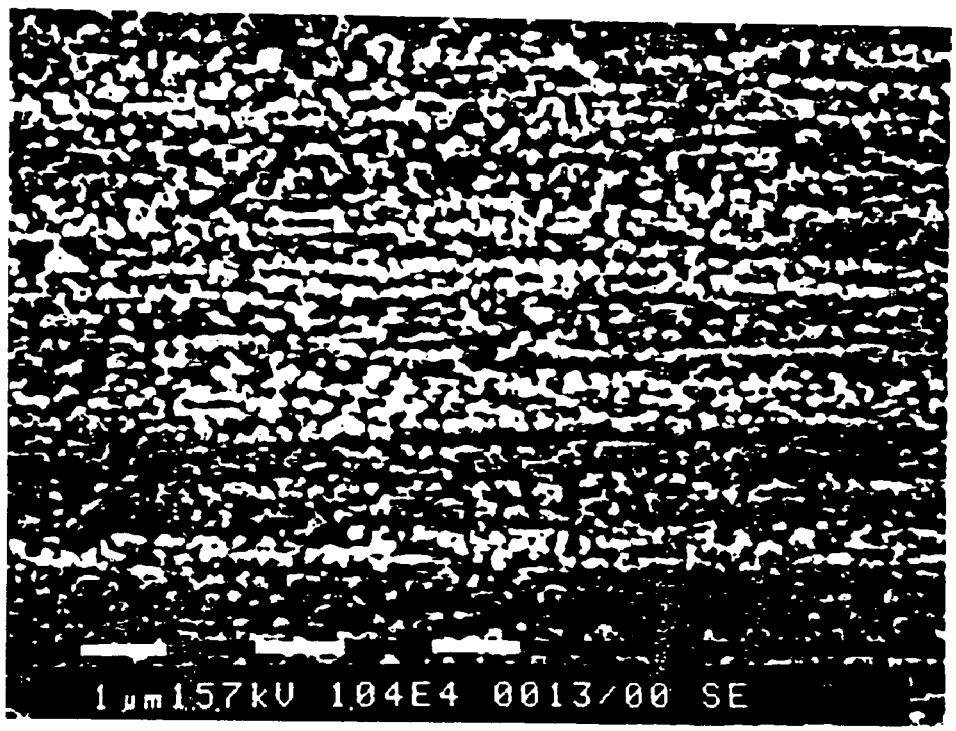
Figure 5:
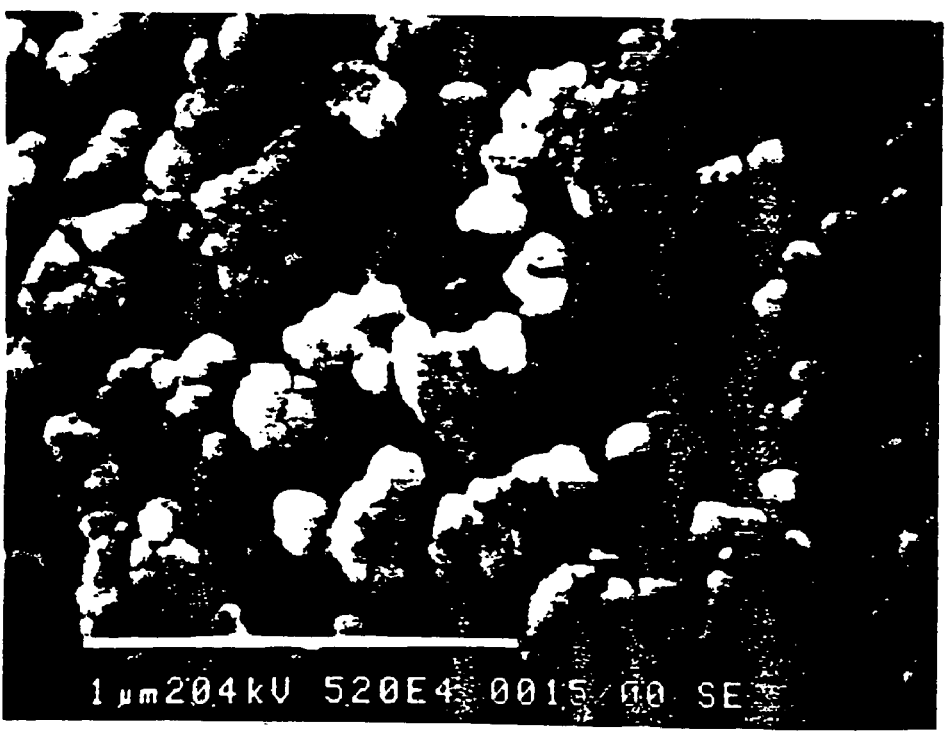
Figure 6:
FIG. 6 is SEM photograph of an untreated implant surface in 52 000 times magnification.
Figure 7:
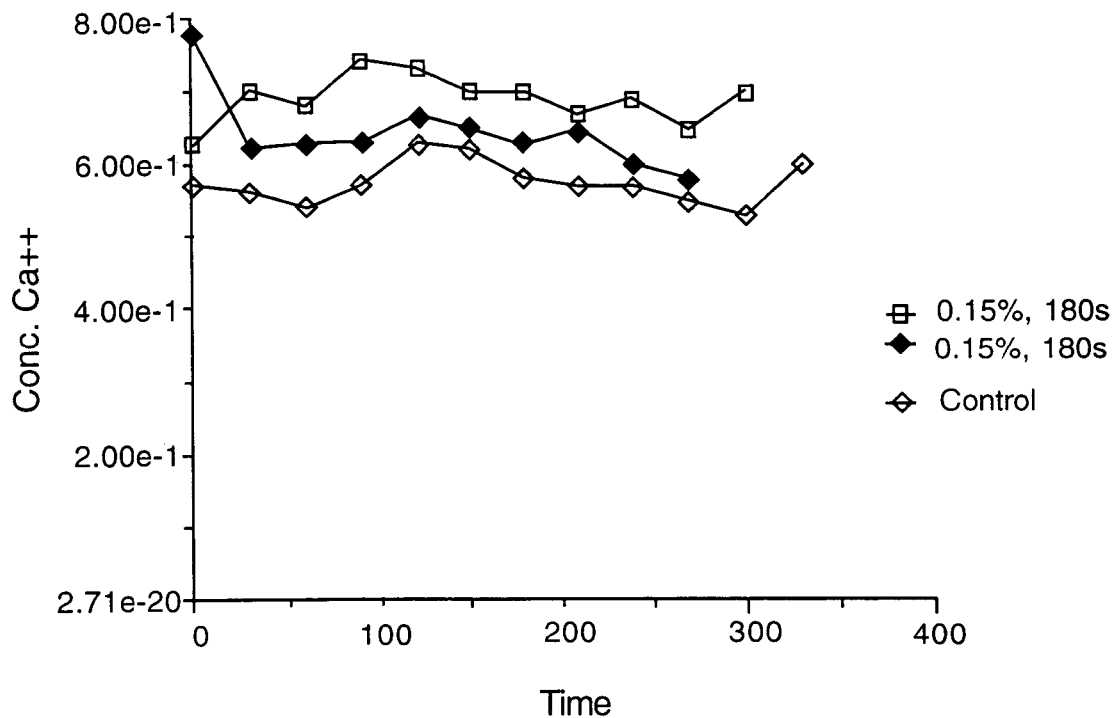
FIGS. 7–9 are diagrams illustrating the effects of different treatments by means of calcium precipitation tests.
Figure 8:
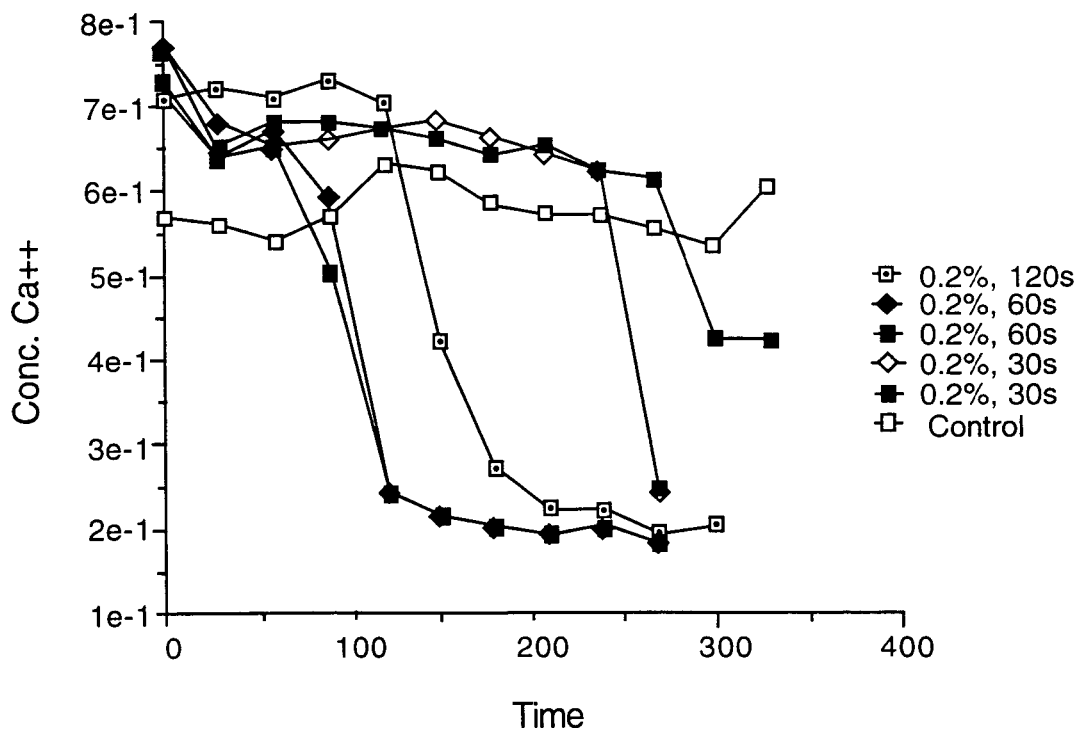
Figure 9:
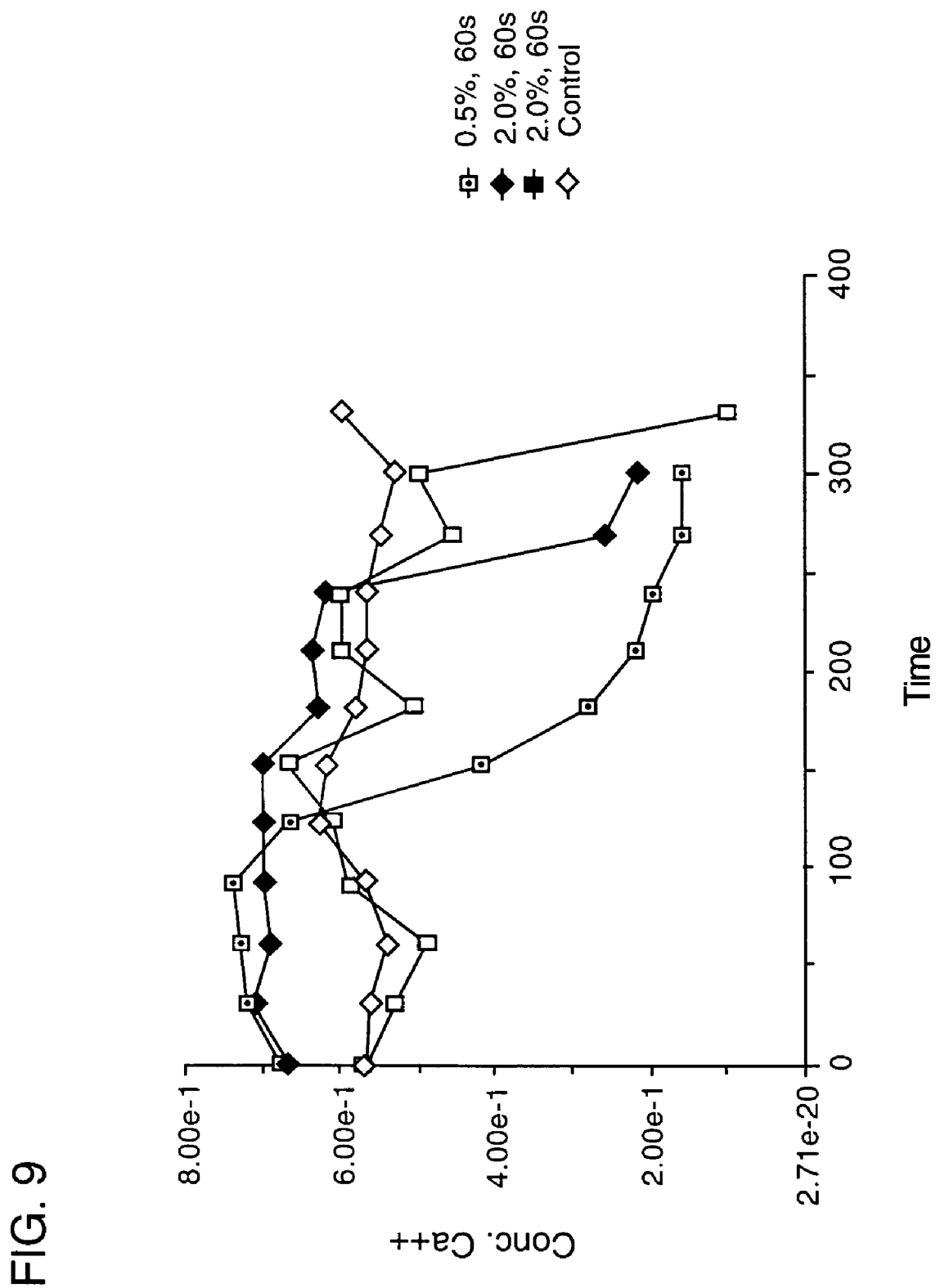

FIG. 3, which shows the surface in FIG. 2 in a magnification of 52 000 times, should be compared with FIG. 6, which shows an untreated surface in a magnification of 52 000 times, and with FIG. 5, which shows the surface of FIG. 4 in a magnification of 52 000 times. As is evident, the surface treated with 0.2% solution is only slightly affected in regard of the morphology, the tooling marks still being discernable, whereas the surface treated for a longer period of time is distinctly altered and covered with a porous layer. It is believed that the best embodiment of the invention involves surfaces whose morphology only are slightly affected by the treatment although other treated surfaces also may have the effect expected from the invention.

In the above push out test implants manufactured and treated in the same way as the reference implant surface were used. It should however be noted that the metallic implants to be sued in the clinical situation and/or in research of course can be manufactured of any metal and treated in any way within the scope of the claims provided the implant surface is equivalent to the reference surface in regard of the content of fluorine.

Example 3

Another way of describing the effect of treatment is by means of the induction of Calcium Phosphate Precipitation. This is an in vitro test described in "Damen, Ten Cate, Ellingsen, Induction of Calcium Precipitation by titanium Dioxide, Journal of Dental Research, October 1991". In this method an implant is immersed in a saturated solution of calcium phosphate. Depending on the surface, precipitation of calcium onto the implant occurs. The concentration of Ca++ is monitored and the time delay (the induction time) until precipitation occurs is measured. The rationale behind this test is the assumption that there is a correlation between the affinity of the implant surface towards the calcium ions and the biocompatibility of the implant surface in bone tissue. The results of the test are illustrated in the appended diagrams, FIGS. 7–10. The concentration of Ca++ is given on the Y-axis (2.00e-1 means $2.00 \times 10^{-1}$ etc). The test time is given on the X-axis in minutes.

The implants in the test had been treated as follows:

| Concentration, | HF Treatment time |
|---|---|
| 0.05% | 180 sec |
| 0.15% | 180 sec |
| 0.2% | 30, 60, 120 sec |
| 0.5% | 60 sec |
| 2.0% | 60 sec |

Untreated control implants were also tested.

The test solution was a solution comprising 7.5 mM $KH_2PO_4$ and 50 mM HEPES (pH 7.2) added to a solution comprising 1 mM $CaCl_2$ and 50 mM HEPES (pH 7.2). HEPES is a standard buffering solution. The temperature of the solution during the tests was 37 degrees centigrade.

The concentration of the calcium in the solution after immersion of the respective implant is measured at a calcium selective electrode during a time period of 5 hours. As indicated in the diagrams, there is no precipitation in solutions in which the control implants and implants treated with 0.15% HF have been immersed during the 5 hour immersion time, see FIG. 7.

For certain of the implants treated with 0.2% HF there was precipitation in the test solution as early as 4 hours after the immersion. These implants had been treated with HF for 60 and 120 sec. Implants having been treated with 0.2% HF for 30 sec caused precipitation, but not until about 5 hours immersion time, see FIG. 8.

Implants treated with 0.5% HF for 60 sec caused precipitation at about 4 hour immersion time, whereas the implants treated with 2.0% HF for 60 sec caused precipitation both before and after 5 hour immersion time.

According to these data there would seem to be ranges of HF concentrations and treatment times giving the desired result, with a central range around 0.2–0.5% giving better results. These data to some extent complement the data in the previous examples, and it consequently is believed that the implants according to the invention also can be defined by means of this test, which is a relatively simple one.

Accordingly, an implant according to the invention can be defined as an implant having been treated with HF and which causes precipitation of calcium ions onto the implant surface from a solution comprising 7.5 mM $KH_2PO_4$ and 50 mM HEPES (pH 7.2) added to a solution comprising 1 mM $CaCl_2$ and 50 mM HEPES (pH 7.2), the temperature of the solution during the tests being 37 degrees centigrade.

Example 4

Screwshaped implants having been implanted into bone tissue in the ulna of rabbits for 2 months were removed by torque and histological studies of the implant surface were made.

For a standard implant treated in 0.2% HF for 120 sec, the bone contact was 63.3%, whereas the bone contact for a standard, untreated control implant was only 42.4%.

For an implant blasted with particles of titanium dioxide and treated in 0.2% HF for 90 sec the bone contact was 53.5% whereas the bone contact for a similarly blasted, but untreated implant was 37.3%.

The above values are mean values for 4–8 implants.

The bone contact was more pronounced in the spongiosa for the treated implants.

The treated implants consequently show a pronounced improvement in comparison with the untreated implants.

What is claimed is:

1. A process of treating a metallic bone implant having no calcium-phosphate-containing coating, consisting essentially of treating the metallic bone implant with an aqueous solution, other than hydrofluoric acid, containing fluoride ions in a concentration of greater than 0% and up to 3%,
    said aqueous solution being free from sodium and sodium ions.

2. A process as claimed in claim 1 wherein said metallic bone implant has a surface constituted by a metallic oxide.

3. A process as claimed in claim 2, wherein said metallic bone implant is constituted by titanium or a titanium alloy, and said metallic oxide is a titanium oxide.

4. A process as claimed in claim 1,
    comprising a further step, performed after said treatment with the aqueous solution containing fluoride ions, of treating the implant with a solution comprising calcium ions to further improve the biocompatibility of the implant.

5. A process as claimed in claim 4 wherein treating with the solution comprising calcium ions, comprises:
    precipitating, onto a surface of the implant, the calcium ions from the solution comprising calcium ions.

6. A process as claimed in claim 4 wherein the metallic bone implant has no calcium-phosphate-containing coating.

7. A process as claimed in claim 4, wherein the solution comprising calcium ions is an aqueous solution of a calcium salt selected from the group consisting of calcium fluoride, calcium phosphate, calcium acetate, and calcium chloride.

8. A process as claimed in claim 7, wherein the solution comprising calcium ions is an aqueous solution of calcium fluoride.

9. A process as claimed in claim 1, wherein the concentration of fluoride ions is from 0.01 to 0.5%.

10. A process as claimed in claim 1, wherein the concentration of fluoride ions is from 0.1 to 0.5%.

11. A process as claimed in claim 1, wherein the concentration of fluoride ions is from 0.2 to 0.5%.

12. A process as claimed in claim 1, wherein the concentration of fluoride ions is approximately 0.2%.

13. A process as claimed in claim 1, wherein said aqueous solution is a solution of a fluoride selected from a group consisting of lithium fluoride, cesium fluoride, potassium fluoride, ammonium fluoride, stannous fluoride, or any combination thereof.

14. A process as claimed in claim 1, wherein treating the metallic bone implant with the aqueous solution comprises retaining a portion of the fluoride ions on a surface of the metallic bone implant, wherein the portion is sufficient to increase a rate of attachment of the metallic bone implant to bone tissue.

* * * * *

UNITED STATES PATENT AND TRADEMARK OFFICE
CERTIFICATE OF CORRECTION

PATENT NO.         : 7,048,870 B1  
APPLICATION NO.    : 09/602528  
DATED              : May 23, 2006  
INVENTOR(S)        : Ellingsen et al.

Page 1 of 1

It is certified that error appears in the above-identified patent and that said Letters Patent is hereby corrected as shown below:

On the Title page,

[*] Notice: Subject to any disclaimer, the term of this patent is extended or adjusted under 35 USC 154(b) by (322) days Delete the phrase "by 322 days" and insert -- by 0 days--

Signed and Sealed this

Fourth Day of September, 2007

JON W. DUDAS  
*Director of the United States Patent and Trademark Office*